(12) United States Patent
Mathias

(10) Patent No.: US 7,305,990 B2
(45) Date of Patent: Dec. 11, 2007

(54) MOUTH GUARD AND KIT

(75) Inventor: Eckart Mathias, Goleta, CA (US)

(73) Assignee: Den-Mat Corporation, Santa Maria, CA (US)

( * ) Notice: Subject to any disclaimer, the term of this patent is extended or adjusted under 35 U.S.C. 154(b) by 151 days.

(21) Appl. No.: 11/014,848

(22) Filed: Dec. 20, 2004

(65) Prior Publication Data

US 2006/0130851 A1     Jun. 22, 2006

(51) Int. Cl.
```
A61F 5/56      (2006.01)
B65D 25/08     (2006.01)
B28B 7/28      (2006.01)
C04B 28/26     (2006.01)
A61B 5/00      (2006.01)
A61C 9/00      (2006.01)
```

(52) U.S. Cl. ............ 128/848; 206/221; 106/38.51; 106/38.3; 433/229; 433/36; 433/37; 433/38

(58) Field of Classification Search ............ 128/859, 128/861, 862; 433/47, 48, 229, 34, 36, 37, 433/90, 89; 106/38, 51, 38.3; 206/221; 523/109

See application file for complete search history.

(56) References Cited

U.S. PATENT DOCUMENTS

| | | | |
|---|---|---|---|
| 3,224,443 A | | 12/1965 | Monaghan |
| 4,063,552 A | * | 12/1977 | Going et al. ............ 128/861 |
| 4,530,662 A | * | 7/1985 | Andersson et al. ......... 433/37 |
| 4,955,393 A | | 9/1990 | Adell |
| 4,983,122 A | * | 1/1991 | Mitnick ................. 433/229 |
| 5,406,963 A | | 4/1995 | Adell |
| 5,562,449 A | * | 10/1996 | Jacobs et al. ............ 433/215 |
| 5,566,684 A | | 10/1996 | Wagner |
| 5,746,221 A | | 5/1998 | Jones et al. |
| 5,816,255 A | | 10/1998 | Fishman et al. |
| 6,082,995 A | | 7/2000 | Wise |
| 6,116,900 A | * | 9/2000 | Ostler ..................... 433/89 |
| 6,354,831 B1 | | 3/2002 | Jensen |
| 6,354,837 B1 | * | 3/2002 | Jensen .................. 433/215 |
| 6,379,147 B1 | * | 4/2002 | Georgakis et al. ......... 433/37 |
| 6,758,671 B2 | * | 7/2004 | Brattesani ................ 433/37 |
| 2002/0144686 A1 | | 10/2002 | Cook |
| 2003/0145863 A1 | | 8/2003 | Fischer et al. |

OTHER PUBLICATIONS

International Search Report, dated Nov. 27, 2006.

* cited by examiner

*Primary Examiner*—Patricia Bianco
*Assistant Examiner*—Tarla Patel
(74) *Attorney, Agent, or Firm*—Crowell & Moring LLP; John W. Ryan; Thomas M. Haas

(57) ABSTRACT

A user-fabricated mouth guard wherein the user's teeth and gums are not directly exposed to the uncured mouth guard material. The uncured mouth guard material is pliant at room temperature and does not have to be heated to form and shape the mouth guard. The cured mouth guard can be pliant or rigid at room temperature. A kit and a method of forming the mouth guard are also disclosed.

11 Claims, 4 Drawing Sheets

MOUTH GUARD AND KIT

BACKGROUND

1. Field of the Invention

The invention relates to the prevention of intraoral and tooth trauma.

2. State of the Art

Facial trauma experienced by athletes has been demonstrably reduced by the use of a mouth guard during participation in athletic events. These mouth guards, or mouth protectors, provide protection against injuries to the teeth, lips, cheeks, and gums, and may also reduce the incidence of head and neck injuries, concussions, and jaw fractures.

A number of mouth guards currently exist in the art for protecting against the injuries described above. The American Society for Testing and Materials has classified mouth guards into three types: stock mouth guards, mouth-formed mouth guards, and custom-fabricated mouth guards. Some of these mouth guards are fitted with a tether or strap to connect them to a fastening point, such as a helmet or the like, to prevent loss, swallowing, or choking on the mouth guard by the user. Generally, mouth protectors are fabricated to cover all teeth of the maxillary arch, except for the erupting third molars. To provide maximum protection, it is believed that the energy absorbed by the mouth protector must be dissipated by the protector, rather than transferred to the underlying tooth and jaw structure.

Stock mouth guards typically can be purchased at sporting goods stores, department stores, and pharmacies. These mouth guards may be made of rubber, polyvinyl chloride, or polyvinyl acetate copolymer and are typically available in small, medium, and large sizes. These stock mouth guards are not in any way molded or "fit" to the persons wearing them and, as a result, can be loose and uncomfortable for the user. Often the mouth must be closed in order to hold them in place, and many athletes find them bulky and uncomfortable. In addition, these mouth guards can interfere with speech and breathing, which is a further strong disincentive for athletes to wear these mouth guards.

Mouth-formed mouth guards are fitted by the user. They are molded to fit the individual wearer either by the use of a moldable inner liner typically of plasticized acrylic gel or silicone rubber, or the use of a moldable thermoplastic that softens when immersed in boiling water and re-hardens when cooled. The thermoplastic mouth guard is also known as the "boil-and-bite" mouth guard. However, repeated biting during participation in athletic events or gnawing due to nervousness before or during an athletic event can cause the material to spread resulting in a loose fit. In addition, aging and/or continual exposure to oral fluids may cause the plasticizers to leach out causing the liner to become hard. The method of forming these mouth guards can also be uncomfortable and difficult for a user to perform. Namely, the user is required to boil the guard for the prescribed amount of time and then insert the hot material into the user's mouth and bite down on it, which can be very uncomfortable. The quality of these mouth guards is clearly highly user-dependant.

Cook, U.S. patent application No. 2002/0144686, describes a "soft" boil-and-bite type of mouth guard. Instead of being made of the traditional ethylene/vinyl acetate (EVA) polymer, it is made of a soft impressionable low-density polyethylene. Wagner, U.S. Pat. No. 5,566,684, describes a mouth guard made of a low softening temperature thermoplastic (e.g., EVA) liner on top of a higher temperature thermoplastic. It is described as a do-it-yourself mouth guard that is formable by the boil-and-bite technique. These mouth guards still suffer from the same disadvantages of traditional boil-and-bite guards.

Another mouth-formed guard is made in a dentist's office by impressing the teeth directly onto an uncured ethyl methacrylate gel, which is laid into an outer mouth guard shell/tray all of which becomes one device. Although the custom fit of the softer "lining" feels more comfortable, some users object to its taste and odor. Instructions for the use of these guards advise that the lining be replaced before every use, and that the actual fitting be done by a dentist, hence, increasing the cost of the guard.

Custom-made mouth guards are considered to be the best of the conventional mouth guards as far as fit, shape retention, and comfort are concerned, but they are also the most expensive. This type of mouth guard tends to be less bulky than the other two types and may stay in position better. Custom mouth guards are typically composed of a thermoplastic polymer, of which the most popular type is ethylene/vinyl acetate copolymer, although acrylic resin, polyurethane, and various rubber materials are also used. Custom-made mouth guards are fabricated by vacuum-drawing a thick thermoplastic film/sheet over a dental mold formed by standard dental impression techniques, and most often this process is done by a dentist or in a dental laboratory. There are usually four steps required in the making of a custom-fit mouth guard: 1) making an impression of the maxillary arch; 2) pouring a cast; 3) forming the thermoplastic material on the cast; and 4) finishing the protector. Because of the special technique used in the dental office, the guards are rather expensive, and still slightly uncomfortable due to the rigidity of the thermoplastic used. Although these mouth guards are reusable, they cannot, ordinarily, be fabricated in the field.

The mouth guards described above are typically U-shaped to match the general shape of the upper dental arch and have upward inner lingual and outer labial walls extending therefrom. Bi-maxillary mouth guards are also available which have protection for both dental arches and hold the mouth in a pre-determined position to allow for maximum breathing capability.

Jones et al., U.S. Pat. No. 5,746,221, teaches a mouth guard made of polytetrafluroethylene or PTFE. The PTFE is cold formable thus it will mold to a user's teeth without being heated. However, the mouth guards of Jones et al. do not cure but remain soft and are easily deformed during use. In fact, Jones et al. teaches the mouth guards are "extremely resistant to hardening" (see col. 6, lines 46-48). A user's teeth and gums directly contact the mouth guard material which the user may find unpleasant and foul tasting.

Going et al., U.S. Pat. No. 4,063,552, teaches a silicone based mouth guard. The mouth guard is formed by squeezing a polydimethyl siloxane material from a packet into a cylindrically shaped dough. The silicone dough is then placed on a U-shaped tray. A user inserts the tray into the mouth and pushes the silicone dough upward to engage the upper teeth. The tray is then removed and the silicone is held in the mouth allowing it to cure. However, significant problems are encountered because the silicone is applied directly to the user's teeth and gums. Firstly, the silicone is forced out above the upper tray edges by the teeth and gums. This material must be reapplied to, for example, along the outside gum surfaces by smoothing it out with the index finger. Also, excess material must be removed. Secondly, the silicone substantially sticks to the tray making it very difficult to remove the tray from within the mouth. To remedy this, Going et al. teach a complex two-part tray equipped with a release liner. Thirdly, undesired chemicals may be absorbed by the user's gums or mucosa due to the direct contact with the uncured silicone, which could lead to skin lesions and rashes in the mouth. The user may also find direct contact with the silicone paste (or putty) unpleasant, foul tasting, and unhygienic.

Fischer et al., U.S. patent application No. 2003/0145863, describes a method of adding an extra cushioning layer to an existing mouth guard by dispensing a curable elastomeric material into the trough of the mouth guard. The device is then placed into a person's mouth to impress the teeth into the material and allowing it to cure, at least partially while inside of the mouth. Fischer et al. discloses that a polysiloxane can be used as the curable elastomeric material. This method suffers from many of the same disadvantages as that of Going et al. Namely, there is direct contact between the user's teeth and gums and the mouth guard material; and the extra cushioning layer material is not prevented from oozing out over the walls surrounding the trough of the mouth guard.

Adell, U.S. Pat. No. 4,955,393, teaches a mouth guard comprising a teeth impressionable liner. The liner can be made of urethanes, silicones, or vinyls and is less rigid than a trough material. A user bites down on the liner, which begins to cure due to the water in a user's saliva. The user then removes the mouth guard and places it in water to complete the curing process. This mouth guard suffers from the same problem of direct contact between the user's teeth and gums and the mouth guard material.

Adell, U.S. Pat. No. 5,406,963, teaches a similar mouth guard and its method of manufacture. This mouth guard comprises a main body and a tooth impressionable liner made of substantially the same material. The materials of the two parts differ only in durometer with the durometer of the main body material being higher than that of the liner material. This mouth guard still suffers from unpleasant direct contact between the user's teeth and gums and the uncured mouth guard material.

Monaghan, U.S. Pat. No. 3,224,443, teaches a method of forming a mouth guard comprising applying a fiber filled silicone putty directly to a user's teeth. The user then works the putty around the teeth using their fingers and tongue and then bites down on the putty to form tooth impressions. The thus formed guard then cures in the mouth. Clearly, a mouth guard formed by this method is prone to thickness differentials and non-uniformities that could lead to injury while in use. Of course, this method also suffers from the problem of direct contact between the silicone putty and the user's teeth and gums which in the extreme could include swallowing and absorbing hazardous curing agents through the gums or mucosa of the user.

Fishman et al., U.S. Pat. No. 5,816,255, describes forming a mouth guard by a similar method except that a bite bar is utilized to hold the putty. A user first measures out equal amounts of a base putty and a catalyst putty. The user then mixes the putty together to form a curable putty. The user then rolls the curable putty into a cylindrically shaped mass and then curves the putty around the bite bar to form a generally U-shaped putty. The putty is then inserted into the user's mouth and the user bites down on the putty and allows it to cure. This mouth guard suffers from the same non-uniformities and direct contact problems as that taught by Monaghan. The method also suffers from relying on the user to perform the cumbersome task of measuring equal amounts of the two putty. Thus, the method is time consuming, frustrating, and the quality of the finished mouth guard is highly user-dependant.

There remains a need for a high quality mouth guard that is relatively inexpensive and readily user-formable. Specifically, there is a need for a user-formable mouth guard that does not require direct contact between the user's teeth and gums, and the uncured mouth guard material.

SUMMARY

One embodiment of the invention is a mouth guard formed by a process wherein a user forms an impression of the user's own teeth in the mouth guard material without the user's teeth or gums being directly exposed to the mouth guard material.

Another embodiment of the invention is a kit for forming a mouth guard. The kit comprises a resin, a thin-walled film container, and a dental tray. The tray and the container are sized to substantially correspond to a user's upper maxillary arch.

Another embodiment of the invention is a method for forming a user-fabricated mouth guard. A resin is provided into a thin-walled container. The container is placed into a dental tray. The resin, container, and tray are inserted into a user's mouth. Impressions of the user's teeth are formed in the resin. The resin is cured. The resin, container, and tray are removed from the user's mouth. The container material is removed from around the cured resin to form a mouth guard.

Another embodiment of the invention is a method for forming a mouth guard. The method comprises forming a mouth guard by using a model of a person's teeth. A resin is provided into a thin-walled container. The container is placed into a tray. The teeth of the model are impressed onto the resin-filled container. The resin is cured. The model of the person's teeth is then lifted off the container. The container material is removed from around the cured resin to form a mouth guard.

The accompanying drawings are for illustrative purposes only. The drawings are not drawn to scale and are not meant to limit the invention in any manner. The scope and breadth of the invention is limited only by the appended claims.

DETAILED DESCRIPTION

The mouth guard of the present invention is a user-fabricated mouth guard made of a polymerizing resin. The mouth guard is formed by the user impressing the user's own teeth into the resin without the user's teeth or gums directly contacting the resin.

The method of formation comprises injecting a polymerizable liquid resin into a thin-walled container; placing the container on a dental tray; inserting the tray into a user's mouth; forming impressions of the user's teeth in the resin; curing the resin; removing the resin, container, and tray from the user's mouth; and removing the container material from around the cured resin to form a mouth guard. This novel mouth guard can also be made by making the dental impression with a stone model of the user's teeth. In either case, the user's teeth and oral tissues do not make direct contact with the uncured elastomeric resin.

The mouth guard of the present invention is formed by the user via a mouth guard kit. The kit comprises a resin delivery device containing a resin; a thin-walled container, and a tray.

Figure 1:
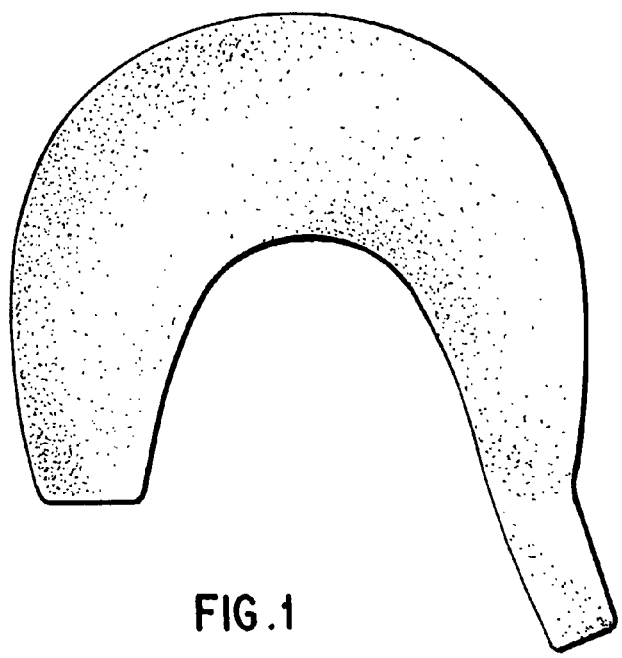
FIG. 1 shows an embodiment of the thin-walled container of the present invention in an empty state.

Turning to FIG. 1, the container is preferably substantially U-shaped, can be made of a thin plastic film, and is open at one end for the introduction of the resin. The container is more preferably a U-shaped plastic bag. The open end extends beyond the closed end of the bag and forms a filling neck. The shape and size of the bag is dictated by the size of the tray that is to be used. Generally, the bag is "oversized" in that it is wider than the trough of the tray, and it has a U-shaped curvature of a larger radius than that of the tray. The bag's shape and size is matched to the design of the tray to be used, i.e., a different bag/tray pair would be used for each of a small, a medium, and a large mouth guard. The bag is preferably made of a clear polyethylene film with a thickness of between about 0.0001 and 0.001 inches. More preferably the polyethylene film has a thickness of between about 0.0002 and 0.0005 inches.

Figure 4:
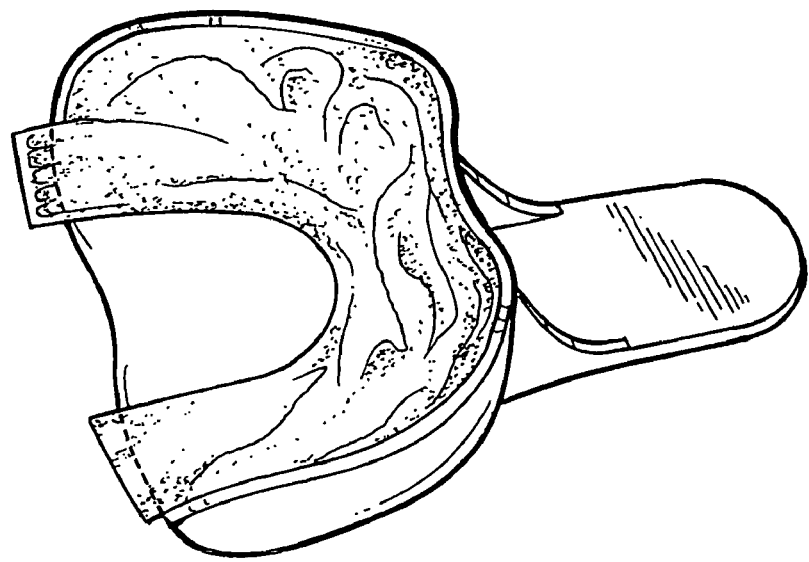
FIG. 4 shows an embodiment of the resin-filled container placed on a tray.

The tray is preferably a regular, inexpensive, plastic tray used in dental offices for taking dental impressions. Preferably, the tray is a conventional dental tray. One embodiment of the dental tray is shown in FIG. 4. Such a tray is designed to fit into a person's mouth and conform to the person's upper maxillary arch. Although these trays are normally sold as disposable, for the purpose of the present invention, the tray is to be reusable. Preferably, the tray is of the non-perforated (solid) type. The tray can be of any size that generally corresponds to the size of a person's mouth and it must match with the appropriate size of U-shaped bag. Any type of dental impression tray will work. In fact, any tray that serves the function and purpose of the tray used in this invention applies.

The resin preferably comprises a liquid, curable elastomeric rubber. More preferably the resin comprises a two-component silicone resin. Most preferably, the resin comprises one part resin and one part curing agent, by volume. However, the ratio of the parts of the composition can be other than 1-to-1, e.g., 1-to-2, 1-to-4, 1-to-10.

The choice of silicone rubber used is based on the intended use of the mouth guard, which may call for different hardness or toughness characteristics. Basically, any elastomeric composition which, when cured, is judged to be sufficiently strong to absorb and dissipate the energy from a sport-type impact can be used.

Other resin compositions that could be used include curable liquids which, when fully cured, are semi-rigid, e.g., 1- or 2-part solventless, liquid, curable compositions, such as polyurethanes, epoxies, polysulfides, and the like, and polyacrylics, poly(methacrylics), polyallylics, and like photocurables.

Figure 2:
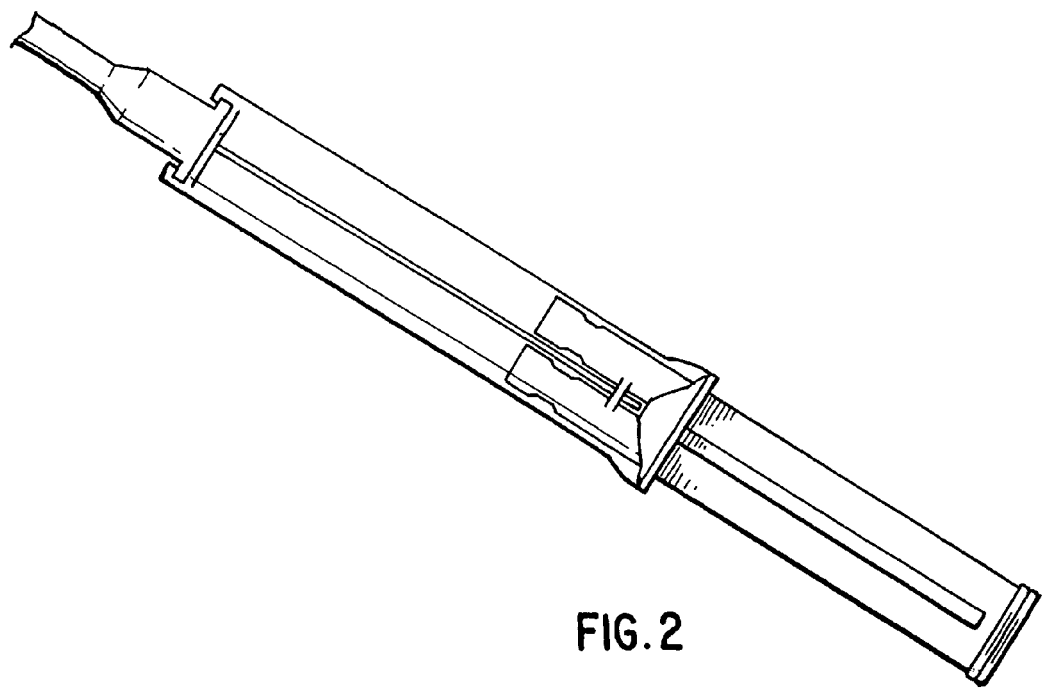
FIG. 2 shows an embodiment of the device used to deliver resin to the container.

The resin is contained within a resin delivery device. Preferably, the resin delivery device is a one-dose syringe, since the range of the quantity needed in the bag is fairly narrow. Preferably, the syringe comprises two separate compartments and a stationary mixing tip. One example of such a syringe is shown in FIG. 2. Such a syringe allows the resin and curing agent to be stored without reacting, and then be delivered to the container when forming the mouth guard. The stationary mixing tip mixes the two components together and delivers a mixture of resin and curing agent to the container. The resin immediately begins to cure after being mixed with the curing agent. Syringes comprising dual cartridges can also be used, but such syringes/cartridges would necessitate a matching dispensing gun.

Method of User-Forming the Mouth Guard

Figure 3:
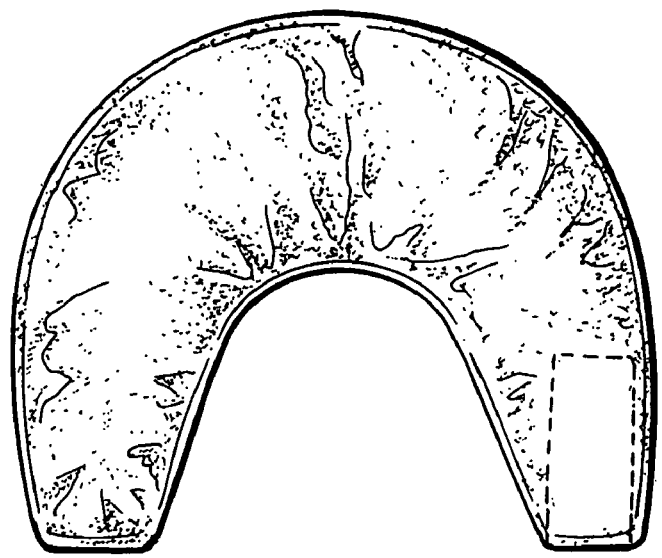
FIG. 3 shows an embodiment of the resin-filled container of the present invention in a closed state.

A user first delivers the resin/curing agent mixture to the U-shaped bag. A user injects the liquid resin into the U-shaped bag by first gathering the bag over the mixer tip, until the tip reaches the closed end of the bag, and then slowly withdrawing the bag from the mixer tip as the bag is being filled without entrapment of large air pockets. The user then preferably evenly distributes the resin throughout the bag by laying the bag onto a work surface and lightly pressing on the bag until it lays flat on the work surface, and all the residual air is displaced out of the bag. The user then closes the filled bag by folding over the filling neck of the bag (once or twice), and leaving it folded under the bag. FIG. 3 shows an embodiment of a resin-filled bag in a closed state.

The user then places the flattened bag into the trough of the plastic dental tray, and again preferably presses lightly on the bag to achieve an even distribution in the tray while insuring that the folded closure lies under the bag. FIG. 4 shows an embodiment of the folded bag placed on a dental tray. Preferably, the bag is positioned into the tray so as to allow the ends of the bag to hangover slightly over the edges of the open ends of the tray.

Figure 5:
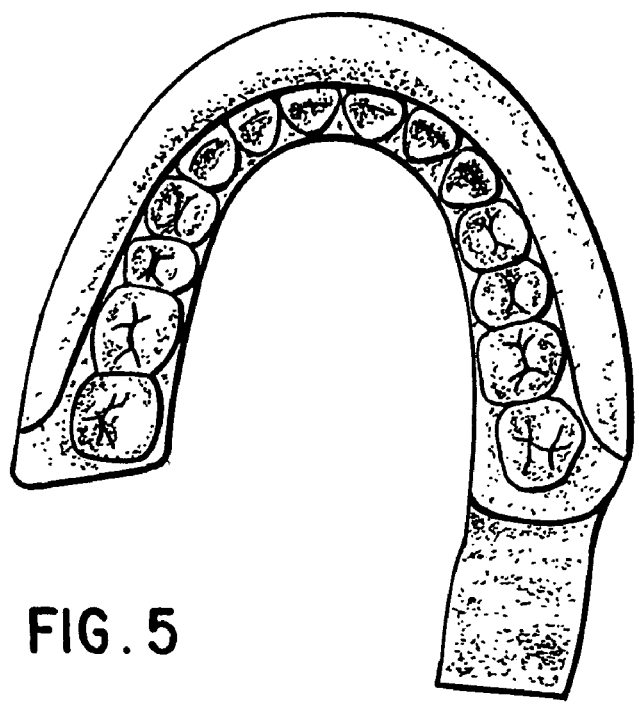
FIGS. 5 and 6 show embodiments of the cured mouth guard of the present invention surrounded by container material.
Figure 6:
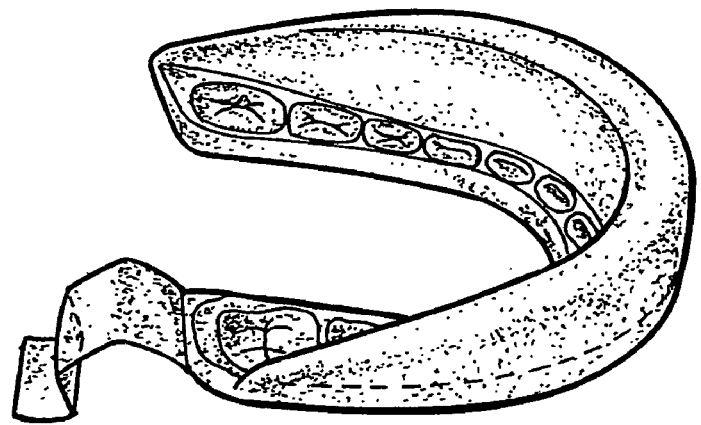
Figure 7:
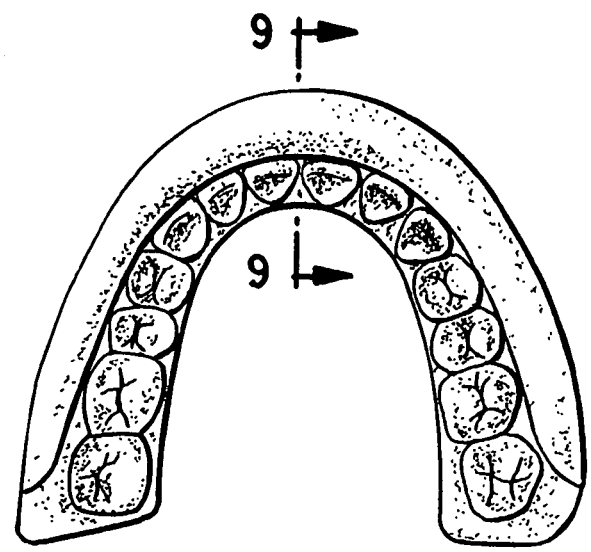
FIGS. 7 and 8 show different views of an embodiment of the cured mouth guard with the container material removed.
Figure 8:
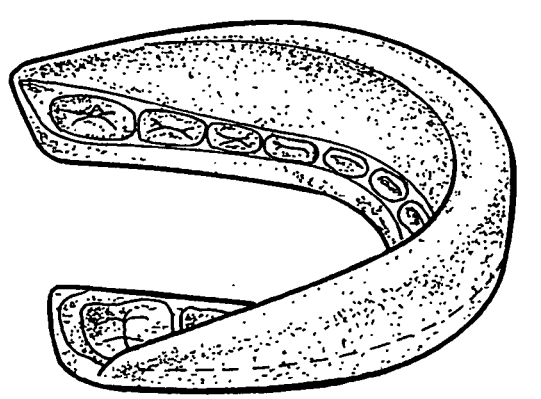
Figure 9:
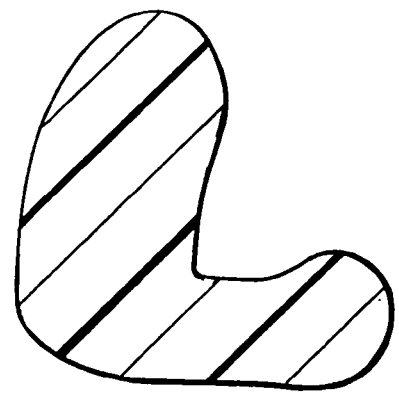
FIG. 9 shows a cross-sectional view, along the line A-A, of the mouth guard shown in FIG. 7.

The user then places the tray with the bag into the user's mouth, and positions the tray to impress the user's upper teeth into the soft resin-filled bag. The user then slowly impresses the teeth by imparting a relaxed yet firm biting pressure on the filled bag. Preferably, the user's palate should just barely touch the palate part of the plastic tray. The pressure forces the liquid resin, surrounded and confined by the bag, to distribute into the unfilled spaces between it and the wall of the plastic tray. The user maintains constant teeth pressure for the time necessary for curing the resin. Once cured, the user removes the tray with the shaped bag from the mouth and rinses both items. FIGS. 5 and 6 show alternative views of the formed mouth guard before the U-shaped bag is removed with the filling neck in an unfolded state. The user then puts aside the tray for re-use, and removes the U-shaped bag from around the cured resin to yield a finished mouth guard. The bag is preferably removed by a peeling action similar to peeling a shrimp. FIGS. 7 and 8 show alternative views of the formed mouth guard after the U-shaped bag has been removed. FIG. 9 shows a cross-sectional view of the finished mouth guard.

The pressure of the user's teeth on the bag forces the uncured/polymerizing resin into the spaces between the row of teeth and the inside wall of the dental tray. Hence, once the resin is cured, this conformation gives rise to the formation of the frontal and lateral walls of the mouth guard, and its overall final shape. The thickness of the biting surfaces, as well as that of the frontal and lateral wall, depends on the dimensions of the bag and the amount of resin used in the bag. The thus formed mouth guard will lessen the risk of injury to the anterior maxillary teeth, lessen the risk of jaw fracture, and reduce the severity of craniofacial injuries, such as damage to the TMJ (temperomandibular joint).

The above description is just one specific embodiment of a method for forming the mouth guard of the present invention. In practice, certain steps such as evenly distributing the resin throughout the bag can be omitted and other steps could be added. The steps can also be performed in any order as long as a cured mouth guard is obtained as the final product. The method is exemplary only and is not meant to limit the invention in any way.

EXAMPLES

Fabrication of the U-shaped Bag

A 0.8-mil clear PE sandwich bag was used as the container starting material. The sandwich bag was laid flat onto a sheet of paper, and a very hot wire which was bent to the shape corresponding to the contour of the desired U-shape was impressed onto the bag. The heat of the wire bonded the two film layers together, and helped "cut" the U-shaped bag away from the rest of the sandwich bag.

Example 1

A tubular U-shaped thin-walled polyethylene bag was filled with 9.81 grams of a 2-part, 1:1 liquid silicone resin (modified/fast Silpak R-2438™), dispensed from a 25 ml dual cartridge operated with a manually held dispensing gun. As soon as the dispensing was completed, the bag was laid on a work bench and the resin was pushed toward the opening of the bag so as to expel the air out of the bag. The filling end of the bag was then folded twice to effectively close the bag. While holding the folded end, the bag was then laid into the trough of a medium-size plastic dental impression tray. The folded closure of the bag was then tucked under the bag at the "open end" of the plastic tray. The bag was pressed gently, and briefly, to achieve an even distribution of the resin in the bag, and to fine-tune the positioning of the bag in the trough.

The tray with the bag was then placed into the user's mouth with the bag facing the upper teeth. The user's upper teeth were impressed carefully into the resin until a resistance was felt indicating that the bag and its contents "tightened up" and resisted further closing of the teeth.

The silicone resin was then allowed to cure while keeping the teeth impressed with a gentle yet firm pressure. Once cured, the tray and the bag containing the finished mouth guard were removed from the user's mouth and rinsed with warm tap water. The mouth guard was taken out of the bag by tearing off the thin polyethylene film. The film was disposed of and the tray was kept for re-use. The bite of the finished guard was about 3-4 mm, and the front inside wall of the guard was about 11-12 mm high. The filling and positioning took about 7 minutes and the total time for forming the guard was about 16 minutes.

Example 2

The procedure of Example 1 was carried out using 10.13 g of a 2-part, 1:1 liquid silicone resin (Ecoflex 5™). The dental tray was slightly modified at its open ends to see if it would make a difference in the closing of the bag, and to see the effects on the dimensions of the final mouth guard. The folded-over closure of the bag did not leak. The bite of the finished guard measured about 5-6 mm, and the front inside wall of the guard was about 9 mm high.

Example 3

Example 2 was carried out using 9.75 g of the same liquid silicone resin, but using a standard medium-size dental impression tray. The bite of the finished guard measured about 3-4 mm, and the front inside wall of the guard was about 10-11 mm high.

Example 4

The procedure of Example 1 was carried out using 9.49 g of the silicone resin, but instead of impressing the teeth by inserting the tray/bag into the mouth, a stone model of a set of upper teeth was impressed onto the bag (while in the tray, resting on a bench top) and held down with a 1.2 kg weight. The bite of the finished guard measured about 4-5 mm, and the front inside wall of the guard was about 9-10 mm high.

Example 5

The procedure of Example 4 was carried out using 9.40 g of a 2-part, 1:1 liquid silicone resin (Dragon Skin Q™). The bite of the finished guard measured about 4 mm, and the front inside wall of the guard was about 10-11 mm high.

Example 6

The procedure of Example 5 was repeated but only 9.10 g of resin was used. The bite of the finished guard measured about 3 mm, and the front inside wall of the guard was about 10-12 mm high.

Example 7

The procedure of Example 5 was repeated using a larger-size bag. 13.61 g of a 2-part, 1:1 liquid silicon resin (modified/fast Silpack R-2458™) was used. The bite of the finished guard measured about 3-4 mm, and the front inside wall of the guard was about 15 mm high.

Example 8

The procedure of Example 7 was repeated but a harder resin was used. 13.60 g of a harder 2-part, 1:1 liquid silicon resin (Silpack R-2458SP™) was used. The bite of the finished guard measured about 3-4 mm, while the inside wall measured about 14-15 mm.

Example 9

The procedure of Example 4 was carried out using 11.69 g of a 2-part, 1:1 liquid polyurethane resin (APTEK 2206™). A weight of approximately 160 g was used for holding down the stone model on the bag. As this resin was not designed for fast curing, it was allowed to cure overnight. The resulting guard had a bite of about 3-4 mm, and an inside wall height of about 10 mm.

Example 10

The procedure of Example 4 was repeated using 10.40 g of a 2-part, 1:1 all-purpose epoxy adhesive (Devcon™). As this resin was not designed for fast curing, it was allowed to cure for two hours. The resulting guard had a bite of about 3 mm, and an inside wall height of about 10 mm.

The fabrication of the mouth guard of the present invention can be performed at home or "on the field". The guard is much more comfortable to wear than over-the-counter stock or boil-and-bite mouth guards, since the material of construction conforms well to the dental impression of the teeth. The cured elastomeric resin is also more compliant and gentle where it makes contact with the gum. The elastomeric compliance also provides easy adaptation to minor imperfections that may result from normal shifting of teeth during normal growth of, for example, a young user.

The thus formed mouth guard is uniform and closely matches the user's own teeth. The user can then use the mouth guard for protection especially in athletic activities in which concussive blows to the head are administered such as boxing, football, and rugby. The mouth guard is tasteless, odorless, reusable, and comparatively inexpensive. Optionally, flavors and colors can be introduced into the resin, and/or into the film of the U-shaped bag. Also, optionally, various ingredients (e.g., antibacterials, antifungals, fluorides, etc,) can be introduced into the resin to give the guard a therapeutic value.

The mouth guards described represent only exemplary embodiments of this invention and are meant in no way to limit the scope of the appended claims. Numerous modifications could be made without departing from the instant inventive concept. For example, the U-shaped bag could be made of a conformable thin elastomeric material. Such material should exhibit a fairly low percentage of elongation so that it limits the amount of stretching to just the desired boundary dictated by the mouth guard design. The bag could be made to contain items which will reinforce the final cured plastic/elastomeric material. For example, the bag could be stuffed with fibrous fillers of sufficient length to allow the injected resin to freely flow within the bag, and "wet" the fibers/fillers thoroughly before curing completely. Such fibrous fillers could include, e.g., low density felt and loosely woven or unwoven fibers/fabrics. A bag with a different closing method could also be used. For example, the "open" end of the bag could constitute a small injector-tip activated one-way valve The injectable elastomer could also include a time-delayed foamable material of acceptable toughness for the particular application. The injectable elastomer could also include light/radiation curable compositions. These materials would be used for curing outside of the users mouth (making use of a light-transparent model of his/her teeth), by placing the filled bag into the trough of a light-transparent tray, and then placing the bag with the mold into a small light-curing box. Of course, the user-formed embodiments could also include an external curing step, such as, slight heating to speed up the curing.

Further, although the embodiments described are for protecting the upper teeth, this inventive process could also be used for lower maxillary mouth guards or bi-maxillary mouth guards.

Although particular embodiments of this invention have been disclosed herein for purposes of explanation, further modifications or variations thereof will be apparent to those skilled in the art to which this invention pertains. Thus, the scope of the present invention is only limited by the appended claims.

What is claimed is:

1. A kit for forming a mouth guard, said kit comprising:
   a thin-walled container, wherein the thin walled container is a u-shaped bag, for holding a curable resin;
   a curable resin; and
   a tray,
   wherein the tray is sized to substantially correspond to a person's upper maxillary arch and
   wherein the u-shaped bag is sized to substantially fit on the tray.

2. The kit of claim 1, wherein the u-shaped bag comprises a polyethylene film.

3. The kit of claim 2, wherein the polyethylene film has a thickness of between about 0.0001 and about 0.001 inches.

4. The kit of claim 1, wherein the u-shaped bag is stuffed with fibrous fillers.

5. The kit of claim 1, wherein the curable resin comprises a two-part resin.

6. The kit of claim 5, wherein the two-part resin comprises a silicone part and a catalytic silicone curing agent part.

7. The kit of claim 6, further comprising a device for delivering the two-part resin.

8. The kit of claim 7, wherein the device comprises separate chambers for each part of the two-part resin, mixing means for mixing the two parts together, and delivery means for delivering the mixed parts to the container.

9. The kit of claim 8, wherein the device comprises a dual cartridge syringe.

10. The kit of claim 6, wherein the two parts are in a ratio of about 1 to about 1 by volume.

11. The kit of claim 1, wherein the u-shaped bag comprises a filling neck.

* * * * *